United States Patent
Caderas

(10) Patent No.: US 7,325,555 B2
(45) Date of Patent: Feb. 5, 2008

(54) RINSING DEVICE FOR A SENSOR PROBE

(75) Inventor: Daniel Caderas, Lohn (CH)

(73) Assignee: Mettler-Toledo AG, Greifensee (CH)

( * ) Notice: Subject to any disclaimer, the term of this patent is extended or adjusted under 35 U.S.C. 154(b) by 393 days.

(21) Appl. No.: 11/075,463

(22) Filed: Mar. 9, 2005

(65) Prior Publication Data

US 2005/0211281 A1 Sep. 29, 2005

Related U.S. Application Data

(63) Continuation of application No. PCT/EP03/50603, filed on Sep. 1, 2003.

(30) Foreign Application Priority Data

Sep. 9, 2002 (DE) .............................. 102 41 833

(51) Int. Cl.
*B08B 3/04* (2006.01)

(52) U.S. Cl. .................... 134/64 R; 134/113; 134/116

(58) Field of Classification Search .............. 134/64 R, 134/113, 116
See application file for complete search history.

(56) References Cited

U.S. PATENT DOCUMENTS

| 3,926,229 | A | * | 12/1975 | Scholle ........................ 141/1 |
| 4,329,649 | A | * | 5/1982 | Scoates ...................... 324/438 |
| 5,011,587 | A |   | 4/1991 | Schmidt ...................... 204/409 |
| 5,460,041 | A | * | 10/1995 | Andes et al. ............. 73/335.08 |
| 5,746,835 | A | * | 5/1998 | Turner et al. ........ 118/723 MW |
| 6,131,473 | A | * | 10/2000 | Hoffman et al. ........... 73/866.5 |
| 6,422,248 | B1 | * | 7/2002 | Furst et al. ............... 134/22.11 |
| 6,517,775 | B1 | * | 2/2003 | Wang et al. .................... 422/3 |
| 6,773,678 | B2 | * | 8/2004 | Cummings et al. ......... 422/104 |

FOREIGN PATENT DOCUMENTS

| CH | 486 906 | * | 4/1970 |
| CH | 673783 |   | 12/1990 |
| EP | 0106858 |   | 5/1984 |
| EP | 0372121 |   | 6/1990 |
| JP | 57-122348 | * | 7/1982 |
| JP | 3-269255 | * | 11/1991 |
| JP | 10019835 |   | 1/1998 |

* cited by examiner

*Primary Examiner*—Frankie L. Stinson
(74) *Attorney, Agent, or Firm*—Standley Law Group LLP

(57) ABSTRACT

A rinsing device for a sensor has a cylinderlike rinsing chamber which has an anterior chamber part connectable to a measuring fluid container and which is configured to receive an immersion tube that contains a sensor and is coaxial with as well as movable along the longitudinal axis L of the rinsing chamber. The rinsing chamber has a rinsing area delimited by an anterior ring groove and a rearward closure. A circumferential wall of the rinsing area has at least one inlet as well as a drainage outlet with an orifice opening for a rinsing medium. The anterior ring groove is aligned at an oblique angle ($\alpha$) to the longitudinal axis, and the orifice opening borders on the most forwardly positioned location of the circumferential wall. The drainage outlet is directed at a forward angle from the orifice opening, and the circumferential wall has an internal diameter which increases continuously from the rearward end of the rinsing area up to the orifice opening.

10 Claims, 2 Drawing Sheets

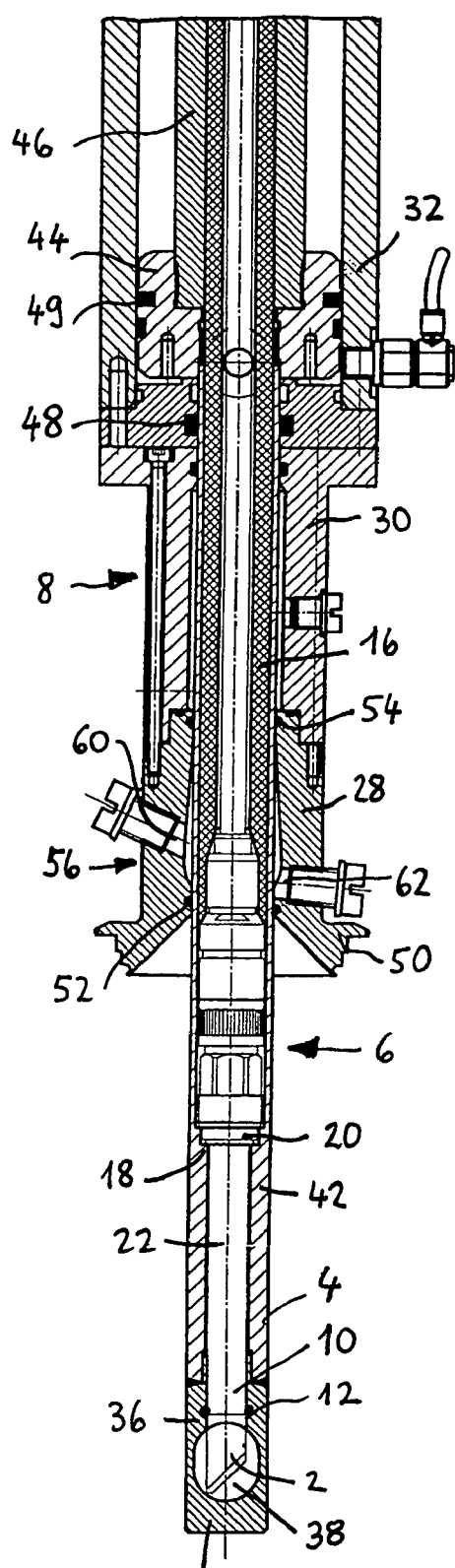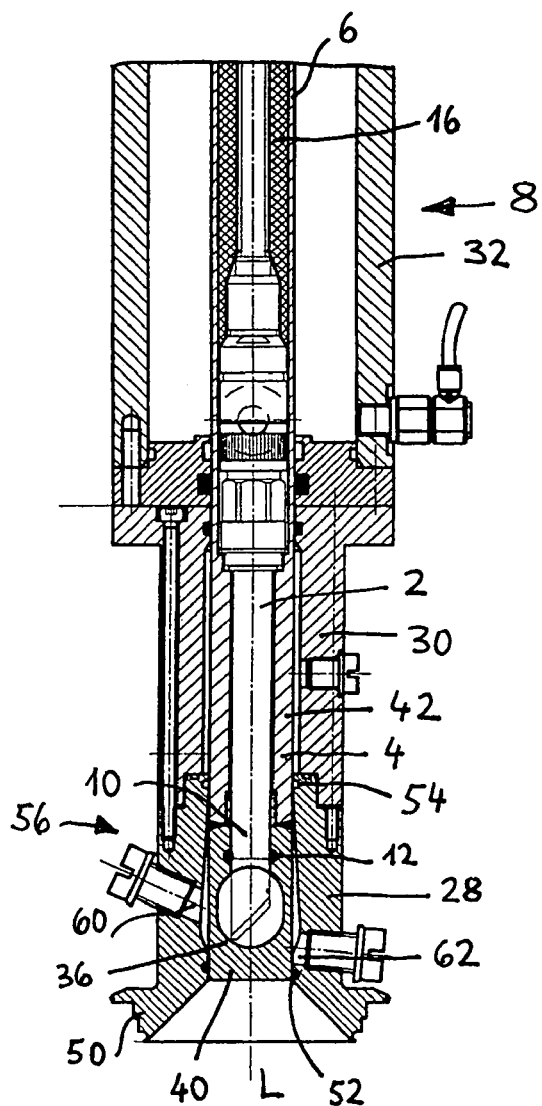
Fig. 1
Fig. 2

RINSING DEVICE FOR A SENSOR PROBE

TECHNICAL FIELD

The invention relates to a rinsing device for a sensor probe.

BACKGROUND OF THE INVENTION

A rinsing device of the kind mentioned above is known, for example, from EP 0 106 858 B1, where a rinsing device is described with a cylindrical rinsing chamber which has an anterior chamber part connectable to a measuring fluid container and which is configured to receive an immersion tube that contains a sensor and is coaxial with and movable along the longitudinal axis of the chamber. The immersion tube is axially movable between a retracted rest position and a deployed working position in order to bring the anterior part of the sensor into contact with the measuring medium in the measuring fluid container. The rinsing chamber has a rinsing area delimited by two ring grooves. The circumferential wall of the rinsing area is equipped with an inlet as well as an outlet for a rinsing medium. In its retracted rest position, the sensor is in the rinsing area where it can be treated with rinsing medium if desired.

The rinsing device described in EP 0 106 858 B1 is part of a probe-holder armature which is installed horizontally in the example shown, i.e., the longitudinal axis of the rinsing chamber is aligned substantially in the horizontal direction. In order to ensure that the rinsing medium is drained as completely as possible from the rinsing chamber, the probe-holder armature is connected to the measuring fluid container in such a way that the drainage outlet is directed downwards, so that the drain orifice is located at the lowest point of the rinsing area. However, if this probe-holder armature is installed vertically or even only close to a vertical position with the sensor extending downward, the rinsing medium can drain off only partially, as the portion of the rinsing medium collected below the drainage outlet will remain in the rinsing chamber. This is highly undesirable for a variety of reasons. For one, a rinse cycle of the sensor as a rule is not performed in one single step in which a single rinsing medium is introduced, but the rinse cycle consists in most cases of a sequence of operations which includes, e.g., a pre-rinse, a treatment with cleaning medium, a post-rinse, a blowing-out with air or a similar procedure, and in some cases a calibration of the sensor by means of appropriate calibration liquids. In a sequence of this kind, as little of the medium as possible should be left in the rinsing chamber after each operation. Furthermore, it should be kept in mind that when the immersion tube is deployed from the rest position into the measuring position, the parts of the immersion tube and the sensor that were in the rinsing area are now entering into the measuring fluid container where they come into contact with the measuring medium. If residual parts of the rinsing medium are taken along, the measuring medium can become contaminated or otherwise compromised.

A possible solution to avoid these problems is found in the probe holder armature according to CH 673 783 A5, which is designed especially for installation in a vertical position. It has a rinsing device that is formed of two rinsing chambers arranged behind each other. With this concept, individual parts of the device can be partitioned off by a kind of sluice-gate arrangement, so that the rinsing medium can be prevented from entering the measuring fluid container, while at the same time the measuring medium can be prevented from escaping into the outer parts of the probe-holder armature. However, the complexity and cost of this rinse chamber are a considerable drawback.

SUMMARY OF THE INVENTION

The task set for the invention is to propose an improved rinsing device to avoid in particular the aforementioned disadvantages.

This task is solved by the rinsing device as defined in the appended claims, with a cylindertike rinsing chamber which has an anterior chamber part connectable to a measuring fluid container and which is configured to receive an immersion tube that contains a sensor and is coaxial with as well as movable along the longitudinal axis of the chamber. The rinsing chamber has a rinsing area delimited by an anterior ring groove and a rearward closure. The circumferential wall of the rinsing area is equipped with at least one inlet as well as an outlet with an orifice opening for a rinsing medium.

Through an arrangement wherein the anterior ring groove is aligned at an oblique angle to the longitudinal axis of the rinsing chamber, wherein the orifice opening is placed directly behind the most forwardly positioned point of the anterior ring groove, wherein further the drain is directed at a forward angle from the orifice opening, and wherein the interior diameter of the circumferential wall increases continuously from the rearward end of the rinsing area to the orifice opening, one can achieve the result that for any orientation, i.e., from a horizontal to a vertical position of the longitudinal axis, the orifice opening will always be located at the lowest point of the rinsing area. Consequently, there is assurance that for any installation within this entire range of positions, substantially all of the rinsing medium can flow out of the rinsing chamber.

Advantageous embodiments of the invention are defined in the dependent claims.

In principle, several different design configurations are possible for the drainage outlet. The drainage outlet according to the claims allows for a particularly simple practical execution being configured as a straight bore hole in which the bore axis is aligned substantially parallel to the plane of the anterior ring groove.

While it is practical in many applications for the axis of the inlet to be directed radially, it can in other cases be useful, as defined in the claims, to add a tangential component to the axis direction of the inlet, in order to achieve a circulatory fluid flow through the rinsing chamber. It can likewise be useful1 if the inlet is designed in accordance with the claims, so that its axis, in the inflow direction, slants towards the forward side of the rinsing device. The rinsing device can be equipped in particular with a plurality of inlets oriented In different directions. A rinsing device can for example have a first inlet with a radial direction as well as a second inlet whose direction has a tangential component. In the latter arrangement, the first inlet serves primarily to rinse off the sensor, while the second inlet serves primarily to flush over the surface portion of the immersion tube wall that lies in the rinsing area.

In principle, the rearward end of the rinsing area can be designed in a variety of different ways. It could be configured, e.g., as a medium-tight movable bellows with a rigid connection to the immersion tube. One embodiment is particularly advantageous, wherein the rearward end of the rinsing area is equipped with a rearward ring groove for an appropriate seal ring.

BRIEF DESCRIPTION OF THE DRAWINGS

Embodiments of the invention will be described below with references to the drawings, wherein:

FIG. 1 represents a lengthwise sectional view of a probe-holder armature with an immersion tube containing a sensor probe in the retracted rest position, including a rinsing device;

FIG. 2 represents a lengthwise sectional view of the probe-holder armature of FIG. 1 in the deployed working position;

DETAILED DESCRIPTION OF PREFERRED EMBODIMENT(S)

Figure 3:
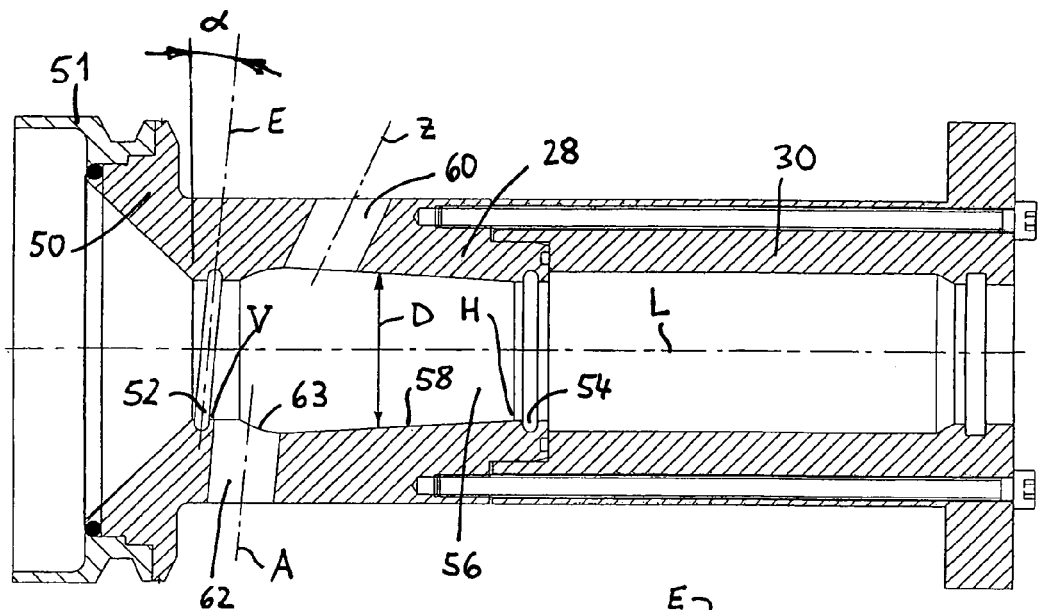
FIG. 3 illustrates the rinsing device of FIG. 1 in a horizontally oriented installation, seen in a lengthwise sectional view.

The probe-holder armature illustrated in FIGS. 1 and 2 contains a sensor 2 which is arranged as a removable device in the forward portion 4 of an immersion tube 6. The immersion tube 6, and along with it the sensor 2, are axially moveable relative to a housing 8 between a retracted rest position and a deployed working position. In the rest position, which is shown in FIG. 1, the immersion tube 6 and the sensor 2 are inside the housing 8. In the working position as shown in FIG. 2, the immersion tube 6 with the sensor 2 is deployed and immersed in a reaction vessel (not shown) to perform measurements in a medium contained in the reaction vessel.

An anterior wall section 10 of the sensor 2 and an O-ring 12 imbedded in the forward portion 4 of the immersion tube 6 form a medium-tight closure of the immersion tube 6. The immersion tube 6 further contains a tubular insert 16 by means of which the sensor 2 in its installed position is pushed against a forward stop 18 of the immersion tube 6. The forward stop 18 in the illustrated example is formed by a narrowing step of the interior diameter of the immersion tube 6 against which the sensor 2 seats itself with a protrusion 20 of the sensor shaft 22.

The housing 8 is composed of several tubular components, i.e., an anterior chamber part 28, an intermediate chamber part 30, a cylindrical housing part 32, as well as a rearward housing part that is not shown in the drawing. The individual chamber parts are connected to each other by connecting flanges and fastening screws.

At its front end, the immersion tube 6 has a cage 36 with at least one lateral opening 38 which in the deployed working condition allows the measuring medium to reach the sensor 2. The cage 36 further has a floor 40 which closes off the front end of the immersion tube. The cage 36 is welded to an intermediate part 42 of the immersion tube. The aforementioned forward stop 18 for the sensor 2 is formed on the inside wall of the intermediate part 42 of the immersion tube. At its opposite end from the cage 36, the intermediate part 42 of the immersion tube is connected to a piston 44 which is supported with axial mobility inside the cylindrical housing part 32. A rearward part 46 of the immersion tube is arranged on the side of the piston 44 that faces away from the intermediate part 42. A plurality of slide bushings 48 and piston seal 49 are provided between the cooperating parts of the housing 8 and the immersion tube 6.

As may be seen in particular in FIG. 3, the anterior chamber part 28 is equipped with a connecting flange 50 through which the probe-holder armature can be joined to a mating flange 51 of the reaction vessel. Since the anterior chamber part 28 is configured as a component of the modular assembly of the housing 8, the probe-holder armature can be attached to reaction vessels with differently dimensioned connecting arrangements by using an anterior chamber part 28 with an appropriately sized connecting flange 50.

The anterior chamber part 28, which is of a cylinderlike shape, if configured as a rinsing chamber which forms a part of a rinsing device for the sensor 2. The rinsing chamber 28 includes a rinsing area 56 delimited by an anterior ring groove 52 and a rearward ring groove 54, with a circumferential wall 58 having an inlet 60 as well as an drainage outlet 62 for a rinsing medium. As a practical matter, the inlet 60 and the drainage outlet 62 are provided with internal screw threads to receive either a corresponding external mating part or, as shown in FIGS. 1 and 2, a closure plug. The latter is useful in particular for performing leak tests. Each of the ring grooves 52, 54 holds a seal ring in tight contact with the exterior wall of the immersion tube 60 to form a medium-tight seal of the rinsing area 56. As can be seen in FIG. 1, when the immersion tube 6 is in the retracted rest position which also represents the rinsing position for the sensor 2, the cage 36 is located within the rinsing area 56. Consequently, rinsing medium supplied through the inlet 60 can enter through the lateral passage opening 38 of the cage 36 to reach the sensor 2 inside the cage 36. The leakage of rinsing medium into the probe-holder armature is prevented by an O-ring 12 that is arranged between the outside wall 10 of the sensor 2 and the inside wall of the immersion tube 6. In the deployed measuring position according to FIG. 2, a part of the immersion tube 6 with no openings is positioned in the anterior chamber part 28 and in particular in the space delimited by the two ring grooves 52 and 54 between the outside wall of the immersion tube 6 and the circumferential wall 58. Accordingly, when the immersion tube 6 is in the deployed working position, the rinsing area 56 is limited to the enclosed space from the ring groove 52 to the ring groove 54 between the outside wall of the immersion tube 6 and the circumferential wall 58.

Figure 4:
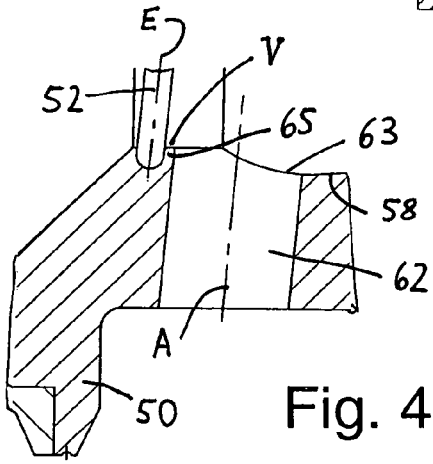
FIG. 4 represents a detail portion of the rinsing device of FIG. 3 in an enlarged view.

To the extent that the design of the rinsing device is essential to its function, it will now be explained in more detail based on the FIGS. 3 and 4. As can be seen in particular in FIG. 3, the anterior ring groove 52 is positioned at an oblique angle to the longitudinal axis L of the rinsing chamber 28. The angle $\alpha$ between the plane E of the ring groove and a plane that extends perpendicular to the longitudinal axis L is about 5°. Based on this obliquely angled arrangement, the circumferential wall 58 of the rinsing area 56 has a most forwardly positioned point V. The orifice opening 63 is arranged immediately behind the most forwardly positioned point V, wherein the qualifier "immediately" means the most forwardly positioned part of the orifice opening 63 borders directly on the anterior ring groove 52 or—as can be seen in FIG. 4—is separated from the anterior ring groove 52 by a wall portion 65 that is very thin in comparison to the other dimensions of the rinsing chamber 28. The drainage outlet 62 in the illustrated example is designed as a straight bore hole whose bore axis A is directed substantially parallel to the plane E of the anterior ring groove 52. The circumferential wall 58 further has an internal diameter D which increases continuously towards the orifice opening 63 from the rearward end H of the rinsing area 58 that is defined by the rearward ring groove 54.

When the probe-holder armature is installed in a horizontal position (as in FIG. 3), i.e., if the longitudinal axis L is oriented horizontally, the widening of the circumferential wall 58 towards the front provides a drainage path for the rinsing medium which is led from all places of the rinsing chamber 28 to the orifice opening 63. As can be seen in FIG. 3, it is an absolute prerequisite that the drainage outlet 62 be directed downward in cases where the probe-holder armature is installed in a horizontal position.

When the probe-holder armature is installed in a vertical position (as in FIGS. 1 and 2), i.e., if the longitudinal axis L is oriented vertically, the obliquely angled anterior ring groove 52 provides a drainage path for the rinsing medium. In this case, the rinsing medium first runs off from all places in the rinsing chamber 28 to the ring groove 52 or, more specifically, to the ring seal seated in the ring groove 52, and is subsequently conducted along the latter to the orifice opening 63.

As can be concluded from the foregoing description, regardless of whether the probe-holder armature is installed in a horizontal or vertical position or in any intermediate position between these two orientations, the rinsing medium contained in the rinsing chamber 28 will flow to the orifice opening 63, as the latter always represents the lowest point of the rinsing chamber. In particular, there are no local pockets in the drainage paths where rinsing medium could accumulate.

The inlet for the rinsing medium can be configured in different ways depending on the application. In particular the position and the angle of inclination of the inlet need to be matched to the arrangement of the passage openings 38 in the cage 36 in order to optimize the flow of rinsing medium to the sensor 2. For example in the rinsing device of FIG. 3, the inlet 60 is arranged in the anterior one-third of the rinsing area 56 with a forward-slanted axis Z.

Figure 5:
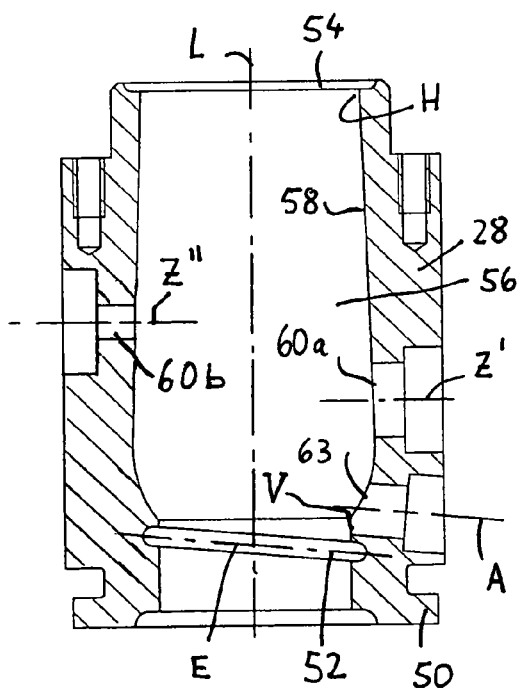
FIG. 5 represents a further rinsing device, installed in a vertical position, seen in a lengthwise sectional view.
Figure 6:
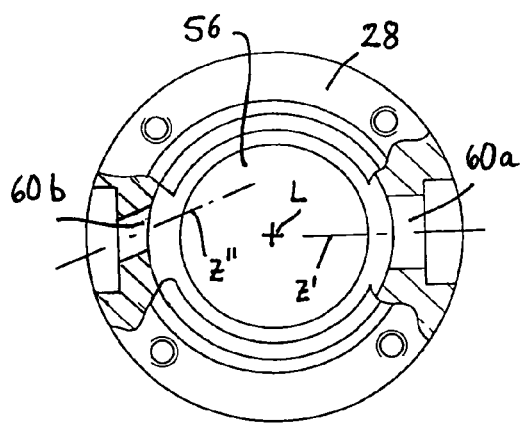
FIG. 6 shows the rinsing device of FIG. 5 in an axially directed, partially cross-sectional view.

FIGS. 5 and 6 show a further configuration of the rinsing device. A first inlet 60a of this rinsing device has an axis Z' directed radially and at a right angle to the longitudinal axis L of the rinsing chamber 28. In contrast, a second inlet 60b which is arranged farther to the rear has a tangential component added to its direction, i.e., the axis Z" of the second inlet 60b is not intersecting the central longitudinal axis L of the rinsing chamber 28. This inlet configuration has the effect that the rinsing medium moves through the rinsing chamber 28 in a spiraling flow pattern. With this arrangement, the first inlet 60a provides an optimal rinsing of the sensor, while the second inlet 60b provides a good flushing around the cage 36.

The term "rinsing medium" in the present context includes not only the actual rinsing liquid such as water. Depending on the application, this term also encompasses a variety of cleaning media, e.g., of the type used in the so-called CIP (cleaning in place) method. Other possible media include steam, rinsing gases, or also calibration fluids. In particular, the inlet 60, 60a, 60b, or in some cases also the drainage outlet 62 can be connected to a sensor-treatment apparatus with the capability to perform an entire sequence of cleaning-, rinsing- and calibrating steps.

The aforementioned angle α between the plane E of the ring groove and a plane that is perpendicular to the longitudinal axis L is preferably about 5°. This ensures on the one hand a good drainage of the rinsing medium while keeping the elliptical elongation of the anterior ring groove sufficiently within limits that a circular seal ring can be used in this ring groove without problems.

The invention claimed is:

1. A rinsing device for a sensor, comprising:
   a cylinderlike rinsing chamber which has an anterior chamber part adapted for connection to a measuring fluid container and adapted for receiving an immersion tube that contains a sensor and is coaxial with, as well as movable along, a longitudinal axis of the rinsing chamber,
   the rinsing chamber having a rinsing area delimited by an anterior ring groove and a rearward closure,
   the rinsing area having a circumferential wall with at least one inlet as well as a drainage outlet with an orifice opening for a rinsing medium,
   the anterior ring groove being aligned at an oblique angle to the longitudinal axis,
   the orifice opening bordering on the most forwardly positioned location of the circumferential wall,
   the drainage outlet being directed at a forward angle from the orifice opening, and
   the circumferential wall having an internal diameter which increases continuously from the rearward end of the rinsing area up to the orifice opening.

2. The rinsing device according to claim 1, wherein the drainage outlet is configured as a straight bore hole in which the bore axis is aligned substantially parallel to the plane of the anterior ring groove.

3. The rinsing device of claim 2, further comprising:
   an inlet with an axis that has a tangentially directed component.

4. The rinsing device of claim 2, further comprising:
   an inlet with an axis which, in the inflow direction, slants towards the forward side of the rinsing device.

5. The rinsing device of claim 2, further comprising:
   a plurality of inlets oriented in different directions.

6. The rinsing device of claim 2, wherein:
   the rearward end of the rinsing area comprises a rearward ring groove.

7. The rinsing device according to claim 1, further comprising:
   an inlet with an axis that has a tangentially directed component.

8. The rinsing device according to claim 1, further comprising:
   an inlet with an axis which, in the inflow direction, slants towards the forward side of the rinsing device.

9. The rinsing device according to claim 1, further comprising:
   a plurality of inlets oriented in different directions.

10. The rinsing device of claim 1, wherein:
    the rearward end of the rinsing area comprises a rearward ring groove.

* * * * *

UNITED STATES PATENT AND TRADEMARK OFFICE
CERTIFICATE OF CORRECTION

PATENT NO. : 7,325,555 B2
APPLICATION NO. : 11/075463
DATED : February 5, 2008
INVENTOR(S) : Caderas It is certified that error appears in the above-identified patent and that said Letters Patent is hereby corrected as shown below:

Column 2, line 7, please delete "cylindertike" and insert -- cylinderlike --.

Column 2, line 42, please delete "usefull" and insert -- useful, --.

Column 2, line 46, please delete "In" and insert -- in --.

Signed and Sealed this

Twentieth Day of May, 2008

JON W. DUDAS
*Director of the United States Patent and Trademark Office*